(12) United States Patent
Sunagawa et al.

(10) Patent No.: US 7,166,750 B1
(45) Date of Patent: Jan. 23, 2007

(54) PROCESS FOR THE PREPARATION OF 5-[(4-CHLOROPHENYL)METHYL]-2,2-DIMETHYLCYCLOPENTANONE

(75) Inventors: Kazuhiko Sunagawa, Fukushima (JP); Hajime Hoshi, Fukushima (JP); Shigeru Mizusawa, Fukushima (JP); Nobuyuki Kusano, Fukushima (JP); Satoru Kumazawa, Fukushima (JP)

(73) Assignee: Kureha Corporation, Tokyo (JP)

( * ) Notice: Subject to any disclaimer, the term of this patent is extended or adjusted under 35 U.S.C. 154(b) by 0 days.

(21) Appl. No.: 10/332,471

(22) PCT Filed: Aug. 11, 2000

(86) PCT No.: PCT/JP00/05401

§ 371 (c)(1),
(2), (4) Date: May 5, 2003

(87) PCT Pub. No.: WO01/12580

PCT Pub. Date: Feb. 22, 2001

(51) Int. Cl.
*C07C 45/00* (2006.01)
*C07C 261/00* (2006.01)
*C07C 69/74* (2006.01)

(52) U.S. Cl. ............ 568/342; 568/346; 560/115; 560/122

(58) Field of Classification Search ........ 568/342, 568/346; 560/115, 122
See application file for complete search history.

(56) References Cited

U.S. PATENT DOCUMENTS

| | | | |
|---|---|---|---|
| 4,938,792 A | 7/1990 | Kumazawa et al. | 71/92 |
| 5,258,404 A * | 11/1993 | Ichinose et al. | 514/522 |
| 5,681,979 A * | 10/1997 | Hoshi et al. | 560/51 |
| 6,344,580 B1 * | 2/2002 | Wong | 558/405 |

FOREIGN PATENT DOCUMENTS

| EP | 267778 | 5/1988 |
|---|---|---|
| EP | 0 329 397 | 8/1989 |
| EP | 413448 | 2/1991 |
| EP | 537909 | 4/1993 |
| EP | 731083 | 9/1996 |

OTHER PUBLICATIONS

Henderson et al. A Quick and Efficient Route to 2-Substituted Cyclopentanones and Cyclohexanones. Synthesis (1983), (12), p. 996-997.*

* cited by examiner

*Primary Examiner*—Sikarl A. Witherspoon
(74) *Attorney, Agent, or Firm*—Nixon & Vanderhye P.C.

(57) ABSTRACT

5-[(4-chlorophenyl)methyl]-2,2-dimethylcyclopentanone is produced by
  reacting 1-[(4-chlorophenyl)methyl]-3-methyl-2-oxocyclopentanecarboxylic acid methyl ester or 1-[(4-chlorophenyl)methyl]-3-methyl-2-oxocyclopentanecarboxylic acid ethyl ester with sodium hydride and methyl halide, then
  hydrolyzing the obtained 1-[(4-chlorophenyl)methyl]-3,3-dimethyl-2-oxocyclopentanecarboxylic acid methyl ester or 1-[(4-chlorophenyl)methyl]-3,3-dimethyl-2-oxocyclopentanecarboxylic acid ethyl ester. The process provides
5-[(4-chlorophenyl)methyl]-2,2-dimethylcyclopentanone, an important intermediate of an agricultural or horticultural fungicide, e.g., Metconazole.

11 Claims, No Drawings

PROCESS FOR THE PREPARATION OF 5-[(4-CHLOROPHENYL)METHYL]-2,2-DIMETHYLCYCLOPENTANONE

This application is the US national phase of international application PCT/JP00/05401 filed Aug. 11, 2000 which designated the U.S.

TECHNICAL FIELD

The present invention relates to a process for producing 5-[(4-chlorophenyl)methyl]-2,2-dimethylcyclopentanone which is an important intermediate of Metconazole as an agricultural or horticultural fungicide.

BACKGROUND ART

In Japanese Patent Application Laid-Open (KOKAI) Nos. 1-93574 (=U.S. Pat. No. 4,938,792) and 1-301664 (=European Patent No. 0329397), there is described 5-[(4-chlorophenyl)methyl]-2,2-dimethylcyclopentanone and 5-[(4-chlorophenyl)methyl]-2,2-dimethyl-1-(1H-1,2,4-triazol-1-yl methyl)cyclopentanol (Metconazole) is derived therefrom by converting the carbonyl group thereof into an epoxy group and then introducing an azolyl group into the epoxidated product. In Japanese Patent Application Laid-Open (KOKAI) No. 1-93574 (=U.S. Pat. No. 4,938,792), as a process for producing 5-[(4-chlorophenyl)methyl]-2,2-dimethylcyclopentanone, a method represented by the following reaction formula (I) is described.

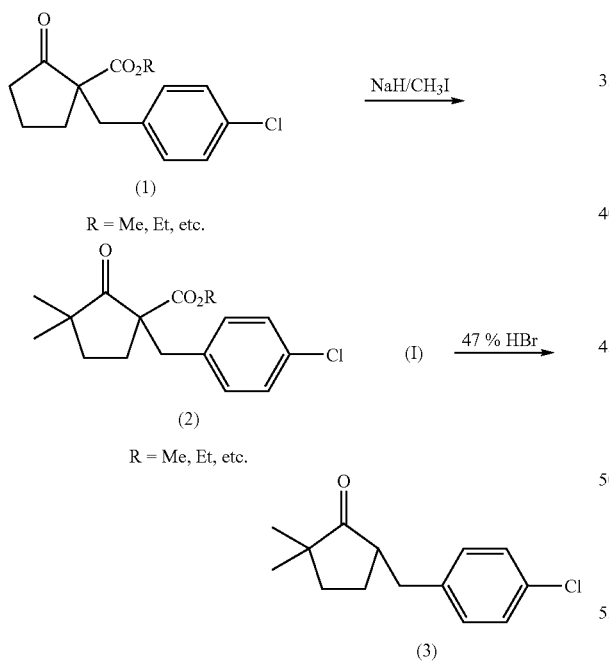

However, in the reaction formula (I), the yield of the compound (2) in the reaction of from the compound (1) to the compound (2) is 81%, the yield of the compound (3) in the reaction of from the compound (2) to the compound (3) is 86%, and, therefore, the total yield of the compound (3) in the reaction of from the compound (1) to the compound (3) is as low as 70%.

Also, in Japanese Patent Application Laid-Open (KOKAI) No. 8-245517 (=U.S. Pat. No. 5,681,979), there is described a method of reacting 1-[(4-chlorophenyl) methyl]-3-methyl-2-oxocyclopentanecarboxylic acid methyl ester with sodium hydroxide and methyl bromide in the presence of molecular sieves to obtain 5-[(4-chlorophenyl) methyl]-2,2-dimethylcyclopentanone as represented by the following reaction formula (II):

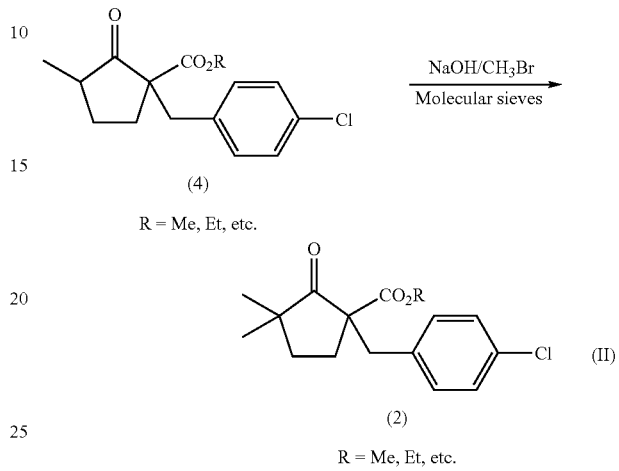

However, in the reaction formula (II), the yield of the compound of the reaction of from the compound (4) to the compound (2) is also as low as 71%.

In the reaction formula (II), when R is isopropyl, the yield is increased to 90% as described. However, since the obtained product (2) [R=isopropyl] has a high resistance to hydrolysis in the subsequent step, the compound (2) is not suitable as a raw material for 5-[(4-chlorophenyl)methyl]-2,2-dimethylcyclopentanone.

Further, in Japanese Patent Application Laid-Open (KOKAI) No. 1-93574 (=U.S. Pat. No. 4,938,792), there is described a method of the production of the above compound (4) in the reaction formula (II), as represented by the following reaction formula (III). However, there is no description about the yield of the compound (4).

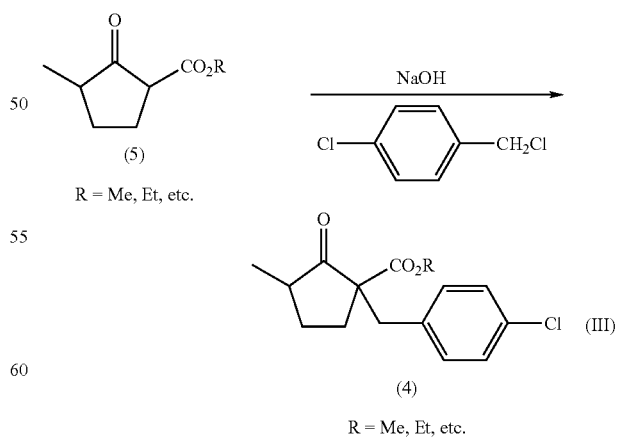

As a method of the production of the compound (5), there is also known the method represented by the following reaction formula (IV), as described in "Precision Organic Synthesis" (published by Nanko-Do Co., Ltd.). However, any of these methods fails to achieve a high yield of the aimed product.

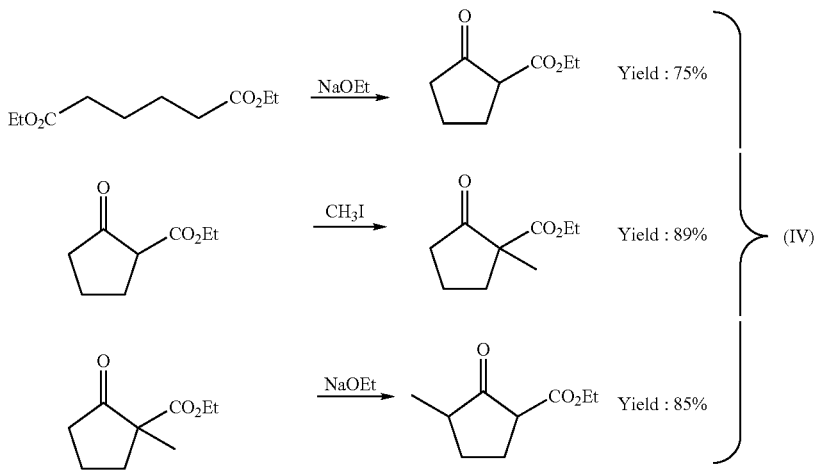

Thus, there is unknown a method of producing 5-[(4-chlorophenyl)methyl]-2,2-dimethylcyclopentanone from dimethyl adipate or diethyl adipate which are industrially readily available, at a high yield. Therefore, it has been required to develop a process for effectively producing the above compound.

DISCLOSURE OF THE INVENTION

Under the above-mentioned circumstance, the present invention has been attained. It is an object of the present invention to provide a simple process for producing high-quality 5-[(4-chlorophenyl)methyl]-2,2-dimethylcyclopentanone which is an important intermediate of Metconazole as an agricultural or horticultural fungicide at a high yield.

As a result of the present inventors' earnest studies, it has been found that by conducting the specific reactions under the specific conditions 1-[(4-chlorophenyl)methyl]-3-methyl-2-oxocyclopentanecarboxylic acid methyl ester or 1-[(4-chlorophenyl)methyl]-3-methyl-2-oxocyclopentanecarboxylic acid ethyl ester obtained from industrially readily available dimethyl adipate or diethyl adipate, it has been found to produce high-quality 5-[(4-chlorophenyl)methyl]-2,2-dimethylcyclopentanone at a high yield. The present invention has been attained based on the findings.

In a first aspect of the present invention, there is provided a process for producing 5-[(4-chlorophenyl)methyl]-2,2-dimethylcyclopentanone, comprising:

reacting 1-[(4-chlorophenyl)methyl]-3-methyl-2-oxocyclopentanecarboxylic acid methyl ester or 1-[(4-chlorophenyl)methyl]-3-methyl-2-oxocyclopentanecarboxylic acid ethyl ester with sodium hydride and methyl halide to obtain 1-[(4-chlorophenyl)methyl]-3,3-dimethyl-2-oxocyclopentanecarboxylic acid methyl ester or 1-[(4-chlorophenyl)methyl]-3,3-dimethyl-2-oxocyclopentanecarboxylic acid ethyl ester; and hydrolyzing the obtained 1-[(4-chlorophenyl)methyl]-3,3-dimethyl-2-oxocyclopentanecarboxylic acid methyl ester or 1-[(4-chlorophenyl)methyl]-3,3-dimethyl-2-oxocyclopentanecarboxylic acid ethyl ester.

In a second aspect of the present invention, there is provided a process for producing 5-[(4-chlorophenyl)methyl]-2,2-dimethylcyclopentanone, comprising:

(1) reacting dimethyl adipate or diethyl adipate with metal alkoxide;

(2) after removing alcohol as produced therefrom, reacting the reaction product obtained with methyl halide;

(3) after completion of the reaction, reacting the reaction product obtained with metal alkoxide;

(4) after removing alcohol as produced therefrom, reacting the reaction product obtained with (4-chlorophenyl) methyl chloride;

(5) reacting 1-[(4-chlorophenyl)methyl]-3-methyl-2-oxocyclopentanecarboxylic acid methyl ester or 1-[(4-chlorophenyl)methyl]-3-methyl-2-oxocyclopentanecarboxylic acid ethyl ester with sodium hydride and methyl halide; and (6) hydrolyzing the obtained 1-[(4-chlorophenyl)methyl]-3,3-dimethyl-2-oxocyclopentanecarboxylic acid methyl ester or 1-[(4-chlorophenyl)methyl]-3,3-dimethyl-2-oxocyclopentanecarboxylic acid ethyl ester.

In a third aspect of the present invention, there is provided a process for producing 1-[(4-chlorophenyl)methyl]-3-methyl-2-oxocyclopentanecarboxylic acid methyl ester or 1-[(4-chlorophenyl)methyl]-3-methyl-2-oxocyclopentanecarboxylic acid ethyl ester, comprising:

(1) reacting dimethyl adipate or diethyl adipate with metal alkoxide;

(2) after removing alcohol as produced therefrom, reacting the reaction product obtained with methyl halide;

(3) after completion of the reaction, reacting the reaction product obtained with metal alkoxide; and (4) after removing alcohol as produced therefrom, reacting the reaction product obtained with (4-chlorophenyl) methyl chloride.

In a fourth aspect of the present invention, there is provided a method of using 5-[(4-chlorophenyl)methyl]-2,2-dimethylcyclopentanone as an intermediate for producing Metconazole, or for producing agricultural or horticultural fungicides.

In a fifth aspect of the present invention, there is provided a method of using 1-[(4-chlorophenyl)methyl]-3-methyl-2-oxocyclopentanecarboxylic acid methyl ester or 1-[(4-chlorophenyl)methyl]-3-methyl-2-oxocyclopentanecarboxylic acid ethyl ester as an intermediate for producing 5-[(4- chlorophenyl)methyl]-2,2-dimethylcyclopentanone, for producing Metconazole, or for producing agricultural or horticultural fungicides.

In a sixth aspect of the present invention, there is provided a method of using as an intermediate for producing 1-[(4-chlorophenyl)methyl]-3,3-dimethyl-2-oxocyclopentanecarboxylic acid methyl ester or 1-[(4-chlorophenyl)methyl]-3,3-dimethyl-2-oxocyclopentanecarboxylic acid ethyl ester, for producing Metconazole, or for producing agricultural or horticultural fungicides.

The present invention will be described in detail below.

In the following descriptions, 1-[(4-chlorophenyl)methyl]-3-methyl-2-oxocyclopentanecarboxylic acid methyl ester and 1-[(4-chlorophenyl)methyl]-3,3-dimethyl-2-oxocyclopentanecarboxylic acid methyl ester are chemically identical to 1-[(4-chlorophenyl)methyl]-3-methyl-2-oxocyclopentanecarboxylic acid ethyl ester and 1-[(4-chlorophenyl)methyl]-3,3-dimethyl-2-oxocyclopentanecarboxylic acid ethyl ester. Therefore, the explanations thereof are made only about the above methyl esters.

The process for the production of 1-[(4-chlorophenyl)methyl]-3-methyl-2-oxocyclopentanecarboxylic acid methyl ester will be described below.

The process for the production of 1-[(4-chlorophenyl)methyl]-3-methyl-2-oxocyclopentanecarboxylic acid methyl ester comprises the following four steps.

First Step (Condensation Ring-Closing Reaction):

Methyl adipate is reacted with metal methoxide. The obtained reaction product is subjected to demethanolation (removal of methanol) to produce a sodium salt of 2-oxocyclopentanecarboxylic acid methyl ester.

Second Step (First Methylation Reaction):

The obtained sodium salt of 2-oxocyclopentanecarboxylic acid methyl ester is reacted with methyl halide to produce 1-methyl-2-oxocyclopentanecarboxylic acid methyl ester.

Third step (Ring-Opening/Condensation Ring-Closing Reactions):

The obtained 1-methyl-2-oxocyclopentanecarboxylic acid methyl ester is reacted with metal methoxide so as to subject the methyl ester to ring-opening and condensation ring-closing reactions, thereby obtaining a sodium salt of 3-methyl-2-oxocyclopentanecarboxylic acid methyl ester.

Fourth step ((4-Chlorophenyl)Methylation Reaction):

The obtained sodium salt of 3-methyl-2-oxocyclopentanecarboxylic acid methyl ester is reacted with (4-chlorophenyl)methyl chloride to produce 1-[(4-chlorophenyl)methyl]-3-methyl-2-oxocyclopentanecarboxylic acid methyl ester.

The above first to fourth steps will be described in detailed below.

Specifically, the 1-[(4-chlorophenyl)methyl]-3-methyl-2-oxocyclopentanecarboxylic acid methyl ester can be produced at a high yield by continuously conducting the above first to fourth steps without any isolation or purification during these steps, under the following operation conditions (amounts charged, reaction conditions, etc.).

First Step:

Since the sodium salt of 2-oxocyclopentanecarboxylic acid methyl ester as the reaction product of the first step is a solid material, the first step is carried out in a solvent. As suitable solvents, aprotic solvents having a boiling point of usually not less than 75° C. may be used in the first step because it is necessary to distil off methanol from the reaction solution. Examples of the solvents may include aromatic compounds such as benzene, toluene, xylene and chlorobenzene; ether-based compounds such as dimethoxyethane and dioxane, or the like. Among these solvents, toluene, xylene and chlorobenzene are preferred.

Dimethyl adipate and metal methoxide are then charged into the solvent. The obtained mixture is heated under ordinary pressure or reduced pressure to distill off methanol together with the solvent. The reaction temperature is usually 70 to 150° C., preferably 80 to 130° C. If required, an additional amount of the solvent is added to the reaction system.

As the metal methoxides, there may be exemplified sodium methoxide, potassium methoxide or the like. Among these metal methoxides, sodium methoxide is preferred. The metal methoxide may be used in the form of either a powder or a methanol solution. The amount of the metal methoxide used is usually 0.9 to 1.0 mole based on one mole of the dimethyl adipate charged. When the amount of the metal methoxide used is less than 0.9 mole, the conversion percentage of the dimethyl adipate may be considerably lowered. When the amount of the metal methoxide used is more than 1.0 mole, the methanol in the reaction system may become difficult to remove, resulting in considerable deterioration in yield.

When the reaction proceeds, the sodium salt of 2-oxocyclopentanecarboxylic acid methyl ester as the reaction product of the first step is precipitated. In order to reduce the viscosity of the obtained slurry and facilitate the stirring thereof, it may be effective to add a small amount of an aprotic polar solvent. As the aprotic polar solvents, there may be exemplified dimethyl sulfoxide (DMSO), N-methyl pyrrolidone, dimethyl imidazoline, dimethyl acetoamide, dimethyl formamide or the like.

In the first step reaction, it is important to sufficiently remove methanol present in the reaction system. If even a very small amount of methanol remains in the reaction system, the yield is considerably deteriorated.

Second Step:

The sodium salt of 2-oxocyclopentanecarboxylic acid methyl ester obtained in the first step is then reacted with methyl halide. The reaction temperature of the second step is usually 50 to 120° C., preferably 70 to 100° C.

As the methyl halides, there may be exemplified methyl chloride, methyl bromide or methyl iodide. The amount of the methyl halide used is usually 0.9 to 1.1 moles based on one mole of dimethyl adipate charged in the first step. When the amount of the methyl halide used is less than 0.9 mole, the reaction may not be completed. When the amount of the methyl halide is more than 1.1 moles, although no adverse influence is exerted on the reaction, further useful effects cannot be expected.

After completion of the reaction, an excess of methyl halide still remaining in the reaction system, if any, is removed by distillation. If the reaction solution still containing the residual methyl halide is subjected to the subsequent step, the metal methoxide added in the subsequent step is considerably consumed, thereby adversely affecting the reaction.

Further, the 1-methyl-2-oxocyclopentanecarboxylic acid methyl ester as the reaction product of the second step has a relatively low boiling point and a high water-solubility. Therefore, when the reaction product is water-washed or the solvent is distilled off at this stage, the yield is considerably deteriorated.

Third Step:

Metal methoxide is then charged into the reaction product obtained in the second step. The obtained mixture is heated under ordinary pressure or reduced pressure to distill off methanol together with the solvent by the same method as used in the first step. The reaction temperature is usually 70 to 150° C., preferably 80 to 130° C. If required, an additional amount of the solvent may be added to the reaction mixture.

As the metal methoxide used in the third step, it is preferred to use the same metal methoxides as used in the first step. The amount of the metal methoxide charged in this step is usually 0.9 to 1.0 mole based on one mole of dimethyl adipate charged in the first step. When the amount of the metal methoxide charged is less than 0.9 mole, the conversion percentage of dimethyl adipate may be considerably reduced. When the amount of the metal methoxide charged is more than 1.0 mole, the removal of methanol in the reaction system may become difficult, resulting in remarkable deterioration in yield.

When the reaction proceeds, the sodium salt of 3-methyl-2-oxocyclopentanecarboxylic acid methyl ester as the reaction product of the third step is precipitated. In order to reduce the viscosity of the obtained slurry and facilitate the stirring thereof, it may be effective to add a small amount of an aprotic polar solvent. As the aprotic polar solvents, there may be exemplified dimethyl sulfoxide (DMSO), N-methyl pyrrolidone, dimethyl imidazoline, dimethyl acetoamide, dimethyl formamide or the like.

In the third step reaction, it is important to sufficiently remove methanol present in the reaction system. If even a very small amount of methanol still remains in the reaction system, the yield of the aimed product is considerably deteriorated.

Fourth Step:

The sodium salt of 3-methyl-2-oxocyclopentanecarboxylic acid methyl ester obtained in third step is then reacted with (4-chlorophenyl)methyl chloride. The reaction temperature is usually 60 to 150° C., preferably 80 to 130° C. The amount of (4-chlorophenyl)methyl chloride used is usually 0.9 to 1.0 mole based on one mole of dimethyl adipate charged in the first step. When the amount of (4-chlorophenyl)methyl chloride used is less than 0.9 mole, the sodium salt of 3-methyl-2-oxocyclopentanecarboxylic acid methyl ester obtained in the third step may remain unconsumed, resulting in deteriorated yield of the aimed product. When the amount of (4-chlorophenyl)methyl chloride used is more than 1.0 mole, an excess of (4-chlorophenyl)methyl chloride added may remain unreacted after completion of the reaction, thereby causing undesired side reactions in the subsequent step.

When the reaction raw materials are completely consumed, the reaction is stopped to wash the reaction product with water and distill off the solvent, thereby isolating high-quality 1-[(4-chlorophenyl)methyl]-3-methyl-2-oxocyclopentanecarboxylic acid methyl ester at a high yield. The thus obtained 1-[(4-chlorophenyl)methyl]-3-methyl-2-oxocyclopentanecarboxylic acid methyl ester has a high boiling point and a low water-solubility. Therefore, the loss when subjected to the above post treatments, will be substantially ignorable.

The process for production of 5-[(4-chlorophenyl)methyl]-2,2-dimethylcyclopentanone will be described below.

The process for producing 5-[(4-chlorophenyl)methyl]-2,2-dimethylcyclopentanone from 1-[(4-chlorophenyl)methyl]-3-methyl-2-oxocyclopentanecarboxylic acid methyl ester, comprises the following two steps.

Fifth Step (Second Methylation Reaction):

The 1-[(4-chlorophenyl)methyl]-3-methyl-2-oxocyclopentanecarboxylic acid methyl ester is then reacted with sodium hydride and methyl halide to produce 1-[(4-chlorophenyl)methyl]-3,3-dimethyl-2-oxocyclopentanecarboxylic acid methyl ester.

Sixth Step (Hydrolysis):

The thus produced 1-[(4-chlorophenyl)methyl]-3,3-dimethyl-2-oxocyclopentanecarboxylic acid methyl ester is hydrolyzed to obtain 5-[(4-chlorophenyl)methyl]-2,2-dimethylcyclopentanone.

The above fifth to sixth steps will be described in detailed below.

More specifically, the process for producing 5-[(4-chlorophenyl)methyl]-2,2-dimethylcyclopentanone at high yield can be accomplished by treating 1-[(4-chlorophenyl)methyl]-3-methyl-2-oxocyclopentanecarboxylic acid methyl ester under the following operation conditions (amounts charged, reaction conditions, etc.).

Fifth Step:

1-[(4-chlorophenyl)methyl]-3-methyl-2-oxocyclopentanecarboxylic acid methyl ester is then reacted with sodium hydride and methyl halide in a solvent at a temperature of usually 60 to 120° C., preferably 80 to 100° C. When the reaction temperature is less than 60° C., the reaction rate may be too low and, therefore, becomes unpractical. When the reaction temperature is more than 120° C., disadvantageous side reactions such as O-alkylation may tend to be frequently caused.

As the solvents, there may be used any aprotic solvents as long as the solvents are non-reactive with sodium hydride or alkyl halide. Examples of the solvents may include aromatic compounds such as benzene, toluene, xylene and chlorobenzene; ether-based compounds such as tetrahydrofuran (THF), dimethoxy ethane and dioxane; aprotic polar compounds such as dimethyl formamide, demethyl acetoamide, N-methyl pyrrolidone and dimethyl sulfoxide, or the like. These solvent may be used alone or in the form of a mixture of any two or more thereof. In particular, the use of a mixed solvent composed of the aromatic compound and the ether-based or aprotic polar compound is preferred.

The amount of the sodium hydride used in the fifth step is usually 1.0 to 1.3 moles, preferably 1.1 to 1.2 moles based on one mole of the 1-[(4-chlorophenyl)methyl]-3-methyl-2-oxocyclopentanecarboxylic acid methyl ester. When the amount of the sodium hydride used is less than 1.0 mole, the reaction may not be completed, resulting in low yield of the aimed product. When the amount of the sodium hydride used is more than 1.3 moles, complicated post-treatments may be required after completion of the reaction.

As the methyl halides, there may be exemplified methyl chloride, methyl bromide or methyl iodide. Among these methyl halides, methyl bromide and methyl iodide are preferred. If methyl bromide is used, a catalytic amount of sodium iodide or potassium iodide may be added thereto. The amount of the methyl halide used is usually 1.0 to 1.3 moles, preferably 1.0 to 1.2 moles based on one mole of the 1-[(4-chlorophenyl)methyl]-3-methyl-2-oxocyclopentanecarboxylic acid methyl ester. When the amount of the metal halide used is less than 1.0 mole, the reaction may not be completed, resulting in low yield of the aimed product. When the amount of the methyl halide used is more than 1.3 moles, the unit of the methyl halide may be deteriorated.

The reaction of this fifth step is a strong exothermic reaction and generates hydrogen. Therefore, it is preferred that after sodium hydride is added to the solvent, 1-[(4-chlorophenyl)methyl]-3-methyl-2-oxocyclopentanecarboxylic acid methyl ester and methyl halide are added to the solvent and reacted with each other while maintaining the temperature of the solvent at the above-specified reaction temperature. After the 1-[(4-chlorophenyl)methyl]-3-methyl-2-oxocyclopentanecarboxylic acid methyl ester as a raw material is dissipated in the reaction system, the obtained reaction mixture is charged into water, washed with water and then subjected to distillation to remove the solvent therefrom, under a nitrogen atmosphere, thereby isolating 1-[(4-chlorophenyl)methyl]-3,3-dimethyl-2-oxocyclopentanecarboxylic acid methyl ester.

Sixth Step:

The hydrolysis and decarboxylation reaction of the 1-[(4-chlorophenyl)methyl]-3,3-dimethyl-2-oxocyclopentanecarboxylic acid methyl ester is conducted at a temperature of from usually 50° C. to a reflux point thereof under either acid or base condition.

In the case where the hydrolysis and decarboxylation reaction is conducted under an acid condition, acetic acid in addition to water may be used as a solvent. Further, catalysts may be added thereto. As the catalysts, there may be used inorganic acids such as hydrochloric acid, hydrobromic acid and sulfuric acid. The hydrolysis and decarboxylation reaction temperature is usually from 50° C. to a reflux point thereof, preferably from 80° C. to the reflux point.

In the case where the hydrolysis and decarboxylation reaction is conducted under a base condition, lower alcohols or aromatic hydrocarbons may be used as a solvent in combination with water. As the bases, there may be used alkali metal hydroxides, preferably sodium hydroxide or potassium hydroxide. The hydrolysis and decarboxylation reaction temperature used under the base condition is from usually 50° C. to a reflux point thereof, preferably from 80° C. to the reflux point.

After the 1-[(4-chlorophenyl)methyl]-3,3-dimethyl-2-oxocyclopentanecarboxylic acid methyl ester as a starting material is dissipated, the obtained reaction mixture is extracted with a solvent, washed with water and subjected to distillation to remove the solvent therefrom, thereby isolating 5-[(4-chlorophenyl)methyl]-2,2-dimethylcyclopentanone. Thereafter, if required, the reaction product is purified by distillation or the like.

BEST MODE FOR CARRYING OUT THE INVENTION

The present invention is described in more detail by Examples, but the following Examples are only illustrative and, therefore, not intended to limit the scope of the present invention thereto.

EXAMPLE 1

One liter of toluene, 174.2 g of dimethyl adipate, 189.1 g of 28% sodium methylate and 15 g of dimethyl formamide (DMF) were charged into a 2-liter four-neck flask, and heated under ordinary pressure while stirring in a nitrogen atmosphere so as to distill off methanol/toluene therefrom. During the heating, 0.5 liter of toluene was added to the flask in an appropriate manner. After methanol was completely distilled-off, the obtained reaction mixture was cooled to 80° C., and 100 g of methyl bromide was dropped into the reaction mixture while maintaining a temperature thereof at 80° C.

After dropping, the reaction mixture was stirred at 80° C. for 2 hours, and then an excess of methyl bromide was distilled off under reduced pressure.

The obtained reaction solution was charged with 187.2 g of 28% sodium methylate and 15 g of dimethyl formamide (DMF). The resultant mixture was heated under ordinary pressure while stirring in a nitrogen atmosphere so as to distill off methanol/toluene therefrom. During the heating, toluene and DMF were appropriately added to the flask in total amounts of 0.5 liter and 15 g, respectively. After methanol was completely distilled-off, the obtained reaction mixture was cooled to 100° C., and then 153 g of (4-chlorophenyl)methyl chloride was dropped into the reaction mixture while maintaining a temperature of the mixture at 100° C.

After dropping, the resultant reaction mixture was refluxed for 3 hours. After completion of the reaction, an organic phase separated was washed with water and subjected to distillation to remove the solvent therefrom, thereby obtaining 277.7 g of a light-yellow oily substance. The purity of the obtained product was measured by gas chromatography. As a result, it was confirmed that the purity of the produced 1-[(4-chlorophenyl)methyl]-3-methyl-2-oxocyclopentanecarboxylic acid methyl ester was 93%, and the yield thereof was 92% based on the methyl adipate charged.

EXAMPLE 2

44.1 g of 60% sodium hydride was charged into a one-liter four-neck flask, and paraffins were removed therefrom by decantation using toluene. Then, 100 ml of toluene, 20 ml of dimethoxy ethane and 1 g of sodium iodide were added to the flask. The flask as reactor was equipped with a condenser filled with dry ice, and immersed in a bath maintained at 80° C. 277.7 g of 1-[(4-chlorophenyl)methyl]-3-methyl-2-oxocyclopentanecarboxylic acid methyl ester obtained in Example 1 and 100 g of methyl bromide are slowly dropped into the flask, so that a strong exothermic reaction was caused while generating hydrogen. 2 hours after dropping, the 1-[(4-chlorophenyl)methyl]-3-methyl-2-oxocyclopentanecarboxylic acid methyl ester was dissipated in the reaction system.

The obtained reaction mixture was introduced into water in a nitrogen atmosphere, and an organic phase was separated from the reaction mixture, washed with water and then subjected to distillation to remove the solvent therefrom, thereby 280 g of a light-yellow oily substance. As a result of measurement of the oily substance by gas chromatography, it was confirmed that the purity of the thus obtained 1-[(4-chlorophenyl)methyl]-3,3-dimethyl-2-oxocyclopentanecarboxylic acid methyl ester was 92%, and the yield thereof was 95% based on 1-[(4-chlorophenyl)methyl]-3-methyl-2-oxocyclopentanecarboxylic acid methyl ester.

EXAMPLE 3

600 ml of acetic acid, 30 ml of water, 70 g of sulfuric acid and 280 g of 1-[(4-chlorophenyl)methyl]-3,3-dimethyl-2-oxocyclopentanecarboxylic acid methyl ester obtained in Example 2 were charged into a one-liter four-neck flask, and stirred at 107° C. for 8 hours. After completion of the reaction, toluene and water were added to the reaction solution, and then an organic phase was separated from the solution, washed with water and then subjected to distillation to remove the solvent therefrom, thereby obtaining a light-yellow oily substance. The obtained oily substance was subjected to simple distillation under a pressure of 1 to 2 mmHg, thereby obtaining 210.2 g of a distillate having a distillation temperature of 120 to 130° C. As a result of measurement of the distillate by gas chromatography, it was confirmed that the purity of the thus obtained 5-[(4-chlorophenyl)methyl]-2,2-dimethylcyclopentanone was 95.5%, and the yield thereof was 97% based on 1-[(4-chlorophenyl)methyl]-3,3-dimethyl-2-oxocyclopentanecarboxylic acid methyl ester.

EXAMPLE 4

500 ml of a 25% sodium hydroxide aqueous solution and 280 g of 1-[(4-chlorophenyl)methyl]-3,3-dimethyl-2-oxocyclopentanecarboxylic acid methyl ester obtained in Example 2 were charged into a one-liter four-neck flask and refluxed for 4 hours. After completion of the reaction, toluene and water were added to the reaction solution, and then an organic phase was separated from the solution, washed with water and then subjected to distillation to remove the solvent therefrom, thereby obtaining a light-yellow oily substance. The obtained oily substance was subjected to simple distillation under a pressure of 1 to 2 mmHg, thereby obtaining 201.6 g of a distillate having a distillation temperature of 120 to 130° C. As a result of measurement of the distillate by gas chromatography, it was confirmed that the purity of the thus obtained 5-[(4-chlorophenyl)methyl]-2,2-dimethylcyclopentanone was 97.5%, and the yield thereof was 95% based on 1-[(4-chlorophenyl)methyl]-3,3-dimethyl-2-oxocyclopentanecarboxylic acid methyl ester.

EXAMPLE 5

The same procedure as defined in Example 1 was conducted except that a sodium methylate powder was used instead of the 28% sodium methylate in the same molar amount as in Example 1. As a result, it was confirmed that the same results as in Example 1 were obtained.

INDUSTRIAL APPLICABILITY

In accordance with the process of the present invention, 5-[(4-chlorophenyl)methyl]-2,2-dimethylcyclopentanone as an important intermediate of an agricultural or horticultural fungicide can be produced with a high quality at a high yield.

What is claimed is:

1. A process for producing 5-[(4-chlorophenyl)methyl]-2,2-dimethylcyclopentanone, comprising:
   (1) reacting dimethyl adipate or diethyl adipate with 0.9 to 1.0 mole of metal alkoxide per mole of dimethyl adipate or diethyl adipate;
   (2) after removing alcohol as produced therefrom in the presence of at least one aprotic solvent, having a boiling point of not less than 75° C., and is selected from the group consisting of an aromatic compound selected from benzene, toluene, xylene and chlorobenzene, and an ether-based compound selected from dimethoxy ethane and dioxane, and in the presence of a small amount of an aprotic polar compound selected from dimethyl sulfoxide, N-methylpyrrolidone, dimethyl imidazoline, dimethyl acetamide and dimethyl formamide, reacting the reaction product obtained with 0.9 to 1.1 moles of methyl halide per mole of dimethyl adipate or diethyl adipate charged in step (1);
   (3) after completion of the reaction, reacting the reaction product obtained with metal alkoxide wherein the amount of the metal alkoxide charged in step (3) is 0.9 to 1.0 mole based on one mole of dimethyl adipate or diethyl adipate charged in step (1);
   (4) after removing alcohol as produced therefrom in the presence of at least one aprotic solvent, having a boiling point of not less than 75° C., and is selected from the group consisting of an aromatic compound selected from benzene, toluene, xylene and chlorobenzene, and an ether-based compound selected from dimethoxy ethane and dioxane, and in the presence of a small amount of an aprotic polar compound selected from dimethyl sulfoxide, N-methylpyrrolidone, dimethyl imidazoline, dimethyl acetamide and dimethyl formamide, reacting the reaction product obtained with 0.9 to 1.0 mole of (4-chlorophenyl) methyl chloride per mole of dimethyl adipate or diethyl adipate charged in step (1);
   wherein the 1-[(4-chlorophenyl)methyl]-3-methyl-2-oxocyclopentanecarboxylic acid methyl ester or ethyl ester is produced by continuously conducting in a single vessel without any isolation or purification of intermediates during steps (1) to (4)
   (5) reacting 1-[(4-chlorophenyl)methyl]-3-methyl-2-oxocyclopentanecarboxylic acid methyl ester or 1-[(4-chlorophenyl)methyl]-3-methyl-2-oxocyclopentanecarboxylic acid ethyl ester with sodium hydride and methyl halide wherein the amount of the sodium hydride used in this reaction is 1.0 to 1.3 moles based on one mole of the 1-[(4-chlorophenyl)methyl]-3-methyl-2-oxocyclopentanecarboxylic acid methyl ester or ethyl ester, and the amount of the methyl halide used is 1.0 to 1.3 moles based on one mole of the 1-[(4-chlorophenyl)methyl]-3-methyl-2-oxocyclopentanecarboxylic acid methyl ester or ethyl ester, and wherein the reaction is conducted in the presence of at least one aprotic solvent, which is non-reactive with sodium hydride or methyl halide, selected from the group consisting of an aromatic compound selected from benzene, toluene, xylene and chlorobenzene, an ether-based compound selected from tetrahydrofuran, dimethoxy ethane and dioxane, and an aprotic polar compound selected from dimethyl formamide, demethyl acetamide, N-methylpyrrolidone and dimethyl sulfoxide; and wherein after sodium hydride is added to the solvent, said ester and methyl halide are added to the solvent; and
   (6) hydrolyzing the obtained 1-[(4-chlorophenyl)methyl]-3,3-dimethyl-2-oxocyclopentanecarboxylic acid methyl ester or 1-[(4-chlorophenyl)methyl]-3,3-dimethyl-2-oxocyclopentanecarboxylic acid ethyl ester.

2. A process for producing 1-[(4-chlorophenyl) methyl]-3-methyl-2-oxocyclopentanecarboxylic acid methyl ester or 1-[(4-chlorophenyl)methyl]-3-methyl-2-oxocyclopentanecarboxylic acid ethyl ester, is produced by:
   (1) reacting dimethyl adipate or diethyl adipate with 0.9 to 1.0 mole of metal alkoxide per mole of dimethyl adipate or diethyl adipate;
   (2) after sufficiently removing alcohol as produced therefrom in the presence of at least one aprotic solvent, having a boiling point of not less than 75° C., and is selected from the group consisting of an aromatic compound selected from benzene, toluene, xylene and chlorobenzene, and an ether-based compound selected from dimethoxy ethane and dioxane, and in the presence of a small amount of an aprotic polar compound, in order to reduce the viscosity of the obtained slurry and facilitate the stirring thereof, selected from dimethyl sulfoxide, N-methylpyrrolidone, dimethyl imidazoline, dimethyl acetamide and dimethyl formamide; reacting the reaction product obtained with 0.9 to 1.1 moles of methyl halide per mole of dimethyl adipate or diethyl adipate charged in step (1);

(3) after completion of the reaction, reacting the reaction product obtained with metal alkoxide wherein the amount of the metal alkoxide charged in step (3) is 0.9 to 1.0 mole based on one mole of dimethyl adipate or diethyl adipate charged in step (1); and (4) after sufficiently removing alcohol as produced therefrom in the presence of at least one aprotic solvent, having a boiling point of not less than 75° C., and is selected from the group consisting of an aromatic compound selected from benzene, toluene, xylene and chlorobenzene, and an ether-based compound selected from dimethoxy ethane and dioxane, and in the presence of a small amount of an aprotic polar compound, in order to reduce the viscosity of the obtained slurry and facilitate the stirring thereof, selected from dimethyl sulfoxide, N-methylpyrrolidone, dimethyl imidazoline, dimethyl acetamide and dimethyl formamide; reacting the reaction product obtained with 0.9 to 1.0 mole of (4-chlorophenyl)methyl chloride per mole of dimethyl adipate or diethyl adipate charged in step (1) wherein the 1-[(4-chlorophenyl)methyl]-3-methyl-2-oxocyclopentanecarboxylic acid methyl ester or ethyl ester is produced by continuously conducting in a single vessel without any isolation or purification of intermediates during steps (1) to (4).

3. A process for producing 1-[(4-chlorophenyl)methyl]-3,3-dimethyl-2-oxocyclopentanecarboxylic acid methyl ester or 1-[(4-chlorophenyl)methyl]-3,3-dimethyl-2-oxocyclopentanecarboxylic acid ethyl ester, comprising:

(1) reacting dimethyl adipate or diethyl adipate with 0.9 to 1.0 mole of metal alkoxide per mole of dimethyl adipate or diethyl adipate;

(2) after removing alcohol as produced therefrom in the presence of at least one aprotic solvent, having a boiling point of not less than 75° C., and is selected from the group consisting of an aromatic compound selected from benzene, toluene, xylene and chlorobenzene, and an ether-based compound selected from dimethoxy ethane and dioxane, and in the presence of a small amount of an aprotic polar compound selected from dimethyl sulfoxide, N-methylpyrrolidone, dimethyl imidazoline, dimethyl acetamide and dimethyl formamide, reacting the reaction product obtained with 0.9 to 1.1 moles of methyl halide per mole of dimethyl adipate or diethyl adipate charged in step (1);

(3) after completion of the reaction, reacting the reaction product obtained with metal alkoxide wherein the amount of the metal alkoxide charged in step (3) is 0.9 to 1.0 mole based on one mole of dimethyl adipate or diethyl adipate charged in step (1);

(4) after removing alcohol as produced therefrom in the presence of at least one aprotic solvent, having a boiling point of not less than 75° C., and is selected from the group consisting of an aromatic compound selected from benzene, toluene, xylene and chlorobenzene, and an ether-based compound selected from dimethoxy ethane and dioxane, and in the presence of a small amount of an aprotic polar compound selected from dimethyl sulfoxide, N-methylpyrrolidone, dimethyl imidazoline, dimethyl acetamide and dimethyl formamide, reacting the reaction product obtained with 0.9 to 1.0 mole of (4-chlorophenyl) methyl chloride per mole of dimethyl adipate or diethyl adipate charged in step (1);

wherein the 1-[(4-chlorophenyl)methyl]-3-methyl-2-oxocyclopentanecarboxylic acid methyl ester or ethyl ester is produced by continuously conducting in a single vessel without any isolation or purification of intermediates during steps (1) to (4)

(5) reacting 1-[(4-chlorophenyl)methyl]-3-methyl-2-oxocyclopentanecarboxylic acid methyl ester or 1-[(4-chlorophenyl)methyl]-3-methyl-2-oxocyclopentanecarboxylic acid ethyl ester, with sodium hydride and methyl halide wherein the amount of the sodium hydride used in this reaction is 1.0 to 1.3 moles based on one mole of the 1-[(4-chlorophenyl)methyl]-3-methyl-2-oxocyclopentanecarboxylic acid methyl ester or ethyl ester, and the amount of the methyl halide used is 1.0 to 1.3 moles based on one mole of the 1-[(4-chlorophenyl)methyl]-3-methyl-2-oxocyclopentanecarboxylic acid methyl ester or ethyl ester, and wherein the reaction is conducted in the presence of at least one aprotic solvent, which is non-reactive with sodium hydride or methyl halide, selected from the group consisting of an aromatic compound selected from benzene, toluene, xylene and chlorobenzene, an ether-based compound selected from tetrahydrofuran, dimethoxy ethane and dioxane, and an aprotic polar compound selected from dimethyl formamide, demethyl acetamide, N-methylpyrrolidone and dimethyl sulfoxide; and wherein after sodium hydride is added to the solvent, said ester and methyl halide are added to the solvent.

4. A process according to claim 1, wherein the 5-[(4-chlorophenyl)methyl]-2,2-dimethylcyclopentanone so produced is thereafter used as an intermediate for producing Metconazole.

5. A process according to claim 2, wherein the 1-[(4-chlorophenyl) methyl]-3-methyl-2-oxocyclopentanecarboxylic acid methyl ester or 1-[(4-chlorophenyl)methyl]-3-methyl-2-oxocyclopentanecarboxylic acid ethyl ester so produced is thereafter used as an intermediate for producing Metconazole.

6. A process according to claim 3, wherein the 1-[(4-chlorophenyl)methyl]-3,3-dimethyl-2-oxocyclopentanecarboxylic acid methyl ester or 1-[(4-chlorophenyl)methyl]-3,3-dimethyl-2-oxocyclopentanecarboxylic acid ethyl ester so produced is thereafter used as an intermediate for producing Metconazole.

7. A process according to claim 2, wherein the 1-[(4-chlorophenyl)methyl]-3-methyl-2-oxocyclopentanecarboxylic acid methyl ester or 1-[(4-chlorophenyl)methyl]-3-methyl-2-oxocyclopentanecarboxylic acid ethyl ester so produced is thereafter used as an intermediate for producing 5-[(4-chlorophenyl)methyl]-2,2-dimethylcyclopentanone.

8. A process according to claim 3, wherein the 1-[(4-chlorophenyl)methyl]-3,3-dimethyl-2-oxocyclopentanecarboxylic acid methyl ester or 1-[(4-chlorophenyl)methyl]-3,3-dimethyl-2-oxocyclopentanecarboxylic acid ethyl ester so produced is thereafter used as an intermediate for producing 5-[(4-chlorophenyl)methyl]-2,2-dimethylcyclopentanone.

9. A process according to claim 1, wherein the 5-[(4-chlorophenyl)methyl]-2,2-dimethylcyclopentanone so produced is thereafter used as an intermediate for producing agricultural or horticultural fungicides.

10. A process according to claim 2, wherein the 1-[(4-chlorophenyl)methyl]-3-methyl-2-oxocyclopentanecarboxylic acid methyl ester or 1-[(4-chlorophenyl)methyl]-3-methyl-2-oxocyclopentanecarboxylic acid ethyl ester so produced is thereafter used as an intermediate for producing agricultural or horticultural fungicides.

11. A process according to claim 3, wherein the 1-[(4-chlorophenyl) methyl]-3,3-dimethyl-2-oxocyclopentanecarboxylic acid methyl ester or 1-[(4-chlorophenyl)methyl]-3,3-dimethyl-2-oxocyclopentanecarboxylic acid ethyl ester so produced is thereafter used as an intermediate for producing agricultural or horticultural fungicides.

* * * * *